United States Patent [19]
Levari

[11] Patent Number: 5,356,401
[45] Date of Patent: Oct. 18, 1994

[54] FRAGRANCE INSERT PANTY UNDERGARMENT

[76] Inventor: Cathy E. Levari, 24972 Express Dr., Laguna Hills, Calif. 92653

[21] Appl. No.: 962,693

[22] Filed: Oct. 19, 1992

[51] Int. Cl.$^5$ .................. A61F 13/15; A61F 13/20
[52] U.S. Cl. .................. 604/359; 604/358; 604/360; 604/385.1; 604/393; 604/396
[58] Field of Search .............. 2/247, 400, 402–403, 2/406; 604/358, 359, 360, 393, 394, 395–397, 402, 333, 345–346

[56] References Cited

U.S. PATENT DOCUMENTS

| | | | |
|---|---|---|---|
| 810,115 | 1/1906 | Green | 604/360 |
| 833,849 | 10/1906 | Schiff | 604/397 |
| 3,489,149 | 1/1970 | Larson | 604/394 |
| 4,037,602 | 7/1977 | Hawthorne | 604/385.1 |
| 4,623,339 | 11/1986 | Ciraldo et al. | 604/360 |
| 5,241,710 | 9/1993 | Lockhart | 604/385.1 |

FOREIGN PATENT DOCUMENTS 3408414  9/1985  Fed. Rep. of Germany .......... 2/406

Primary Examiner—Randall L. Green
Assistant Examiner—P. Zuttarelli
Attorney, Agent, or Firm—E. Michael Combs

[57] ABSTRACT

An undergarment is arranged to have a continuous body panel to include a front panel and rear panel, with an elastomeric band at an upper end of the body panel, and a crotch web connecting lowermost ends of the body panel, and more specifically the front and rear panels together, with right and left leg openings directed through the body panel between the front and rear panels. A pocket member accessed through a flap is provided, with the pocket member flap selectively securable to the lowermost portion of the front panel to receive a flexible fibrous insert web having a fluid fragrance saturated therewithin.

1 Claim, 4 Drawing Sheets

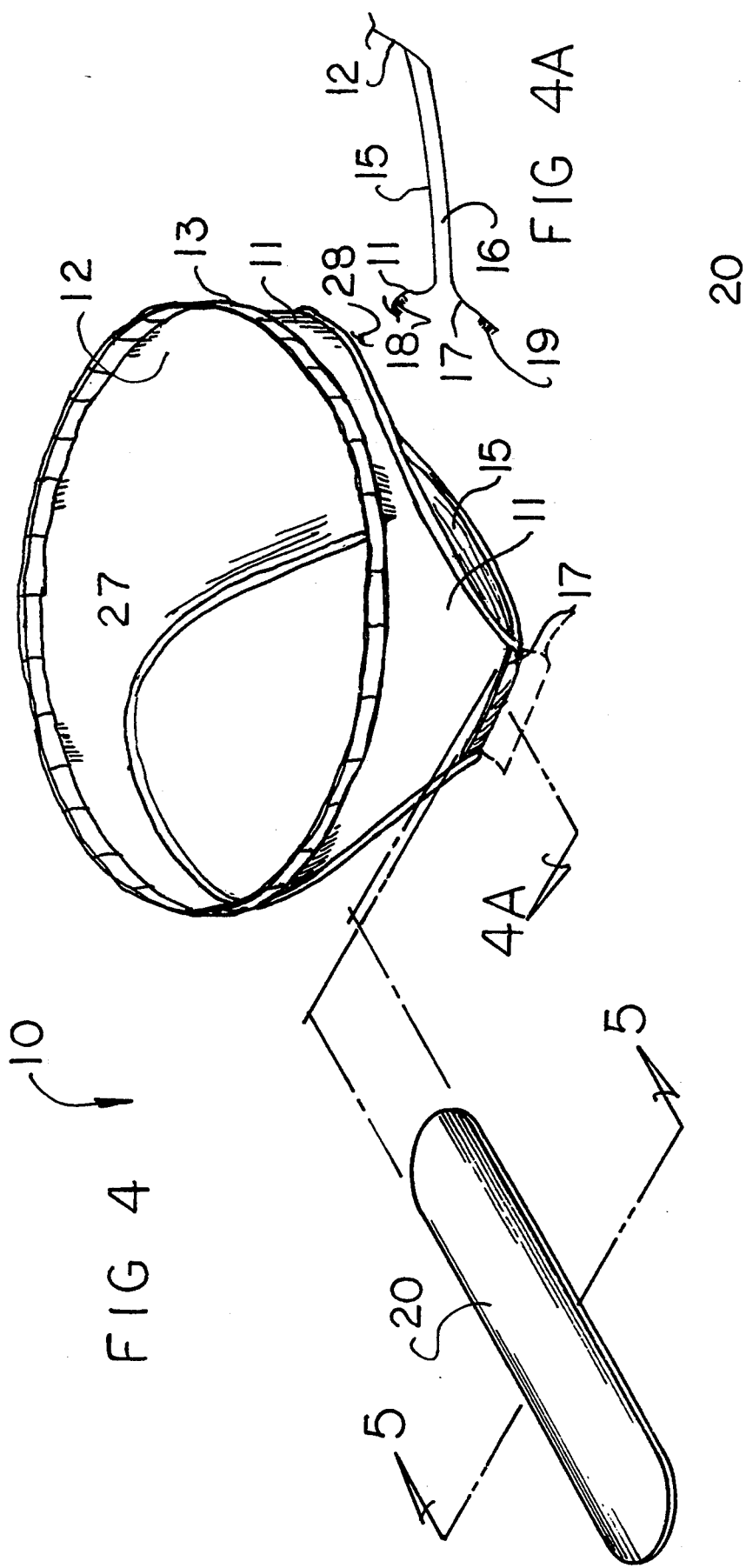

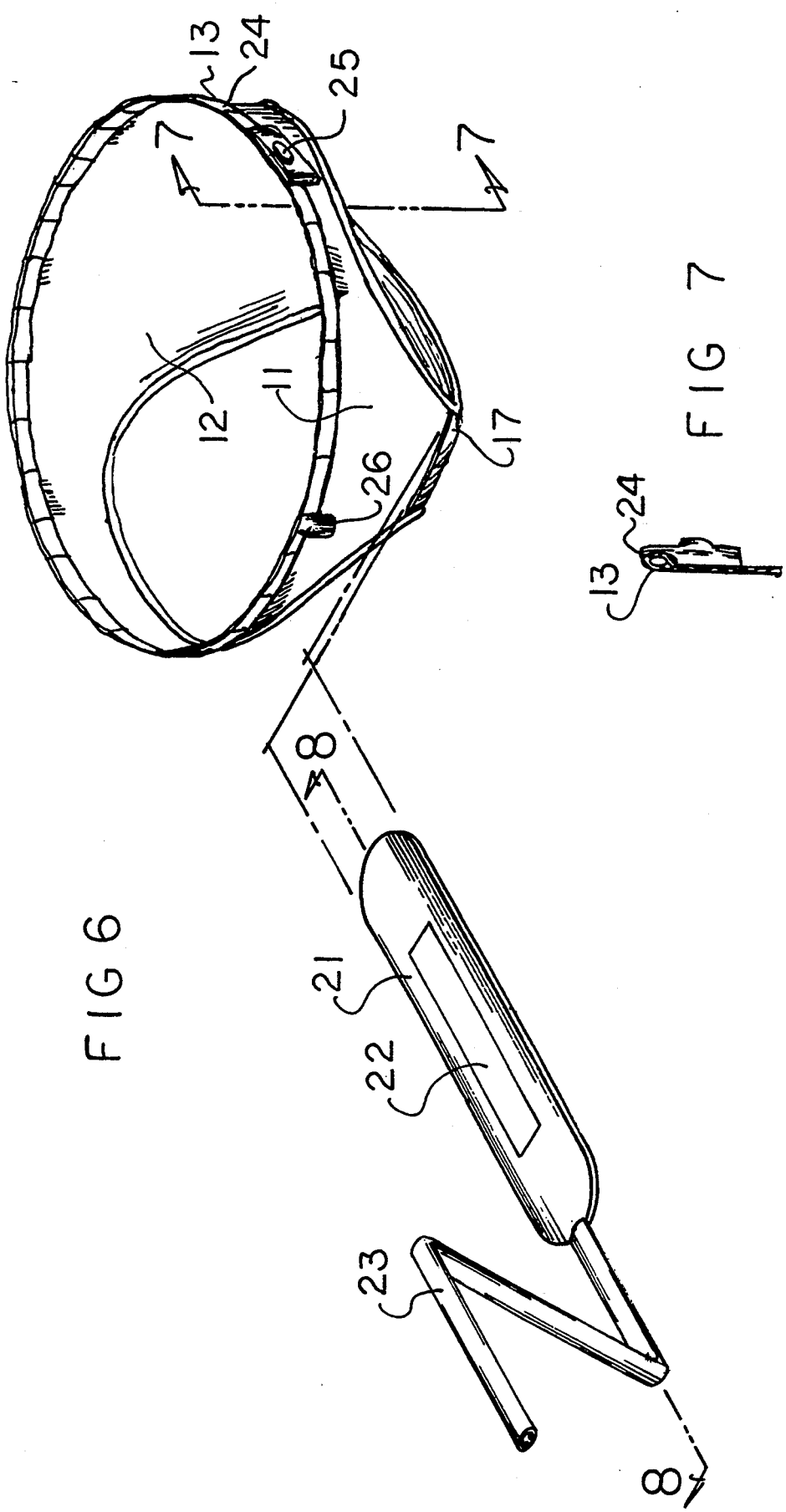

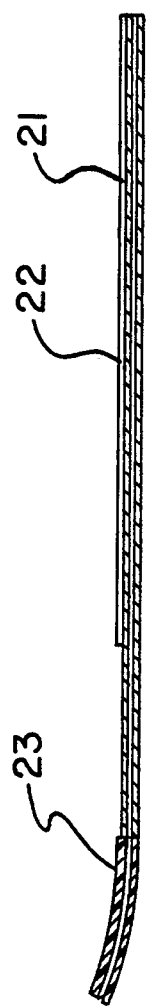
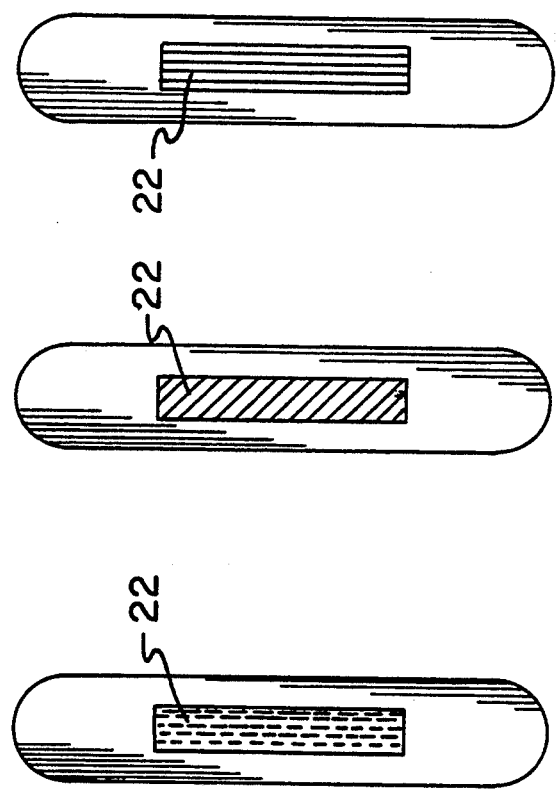
FIG. 8
FIG. 9  FIG. 10  FIG. 11

FRAGRANCE INSERT PANTY UNDERGARMENT

BACKGROUND OF THE INVENTION

1. Field of the Invention

The field of invention relates to undergarment structure, and more particularly pertains to a new and improved fragrance insert panty undergarment wherein the same is arranged to receive and secure a fragrance dispensing web within a crotch portion of the undergarment.

2. Description of the Prior Art

Undergarment arrangements of various types typically utilized in the prior art have been in the form of panty liners arranged for mounting within an associated panty structure. Such liner structure is exemplified in the U.S. Pat. Nos. 4,648,876; 4,347,092; 4,950,264; 4,795,455; and 4,654,038.

Accordingly, it may be appreciated there continues to be a need for a new and improved fragrance insert panty undergarment as set forth by the instant invention which addresses both the problems of ease of use as well as effectiveness in construction to direct a fragrance fluid through a crotch portion of a panty undergarment and in this respect, the present invention substantially fulfills this need.

SUMMARY OF THE INVENTION

In view of the foregoing disadvantages inherent in the known types of undergarment structure now present in the prior art, the present invention provides a fragrance insert panty undergarment wherein the same includes a crotch web having a pocket coextensive therewith to receive a fragrance dispensing fibrous web therewithin. As such, the general purpose of the present invention, which will be described subsequently in greater detail, is to provide a new and improved fragrance insert panty undergarment which has all the advantages of the prior art undergarment structure and none of the disadvantages.

To attain this, the present invention provides an undergarment arranged to have a continuous body panel to include a front panel and rear panel, with an elastomeric band at an upper end of the body panel, and a crotch web connecting lowermost ends of the body panel, and more specifically the front and rear panels together, with right and left leg openings directed through the body panel between the front and rear panels. A pocket member accessed through a flap is provided, with the pocket member flap selectively securable to the lowermost portion of the front panel to receive a flexible fibrous insert web having a fluid fragrance saturated therewithin.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved fragrance insert panty undergarment which has all the advantages of the prior art undergarment structure and none of the disadvantages.

It is another object of the present invention to provide a new and improved fragrance insert panty undergarment which may be easily and efficiently manufactured and marketed.

It is a further object of the present invention to provide a new and improved fragrance insert panty undergarment which is of a durable and reliable construction.

An even further object of the present invention is to provide a new and improved fragrance insert panty undergarment which is susceptible of a low cost of manufacture with regard to both materials and labor, and which accordingly is then susceptible of low prices of sale to the consuming public, thereby making such fragrance insert panty undergarment economically available to the buying public.

Still yet another object of the present invention is to provide a new and improved fragrance insert panty undergarment which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 4 is an isometric illustration of the instant invention.

FIG. 4a is an orthographic view, taken along the lines 4a—4a of FIG. 4 in the direction indicated by the arrows.

FIG. 5 is an orthographic view, taken along the lines 5—5 of FIG. 4 in the direction indicated by the arrows.

FIG. 6 is an isometric illustration of a modified aspect of the invention.

FIG. 7 is an orthographic view, taken along the lines 7—7 of FIG. 6 in the direction indicated by the arrows.

FIG. 8 is an orthographic view, taken along the lines 8—8 of FIG. 6 in the direction indicated by the arrows.

FIGS. 9, 10, and 11 are orthographic top views of color coded insert webs utilized by the invention.

DESCRIPTION OF THE PREFERRED EMBODIMENT

Figure 1:
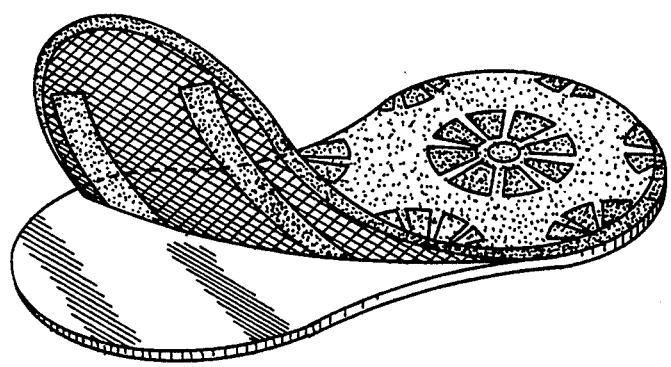
FIG. 1 is an isometric illustration of a prior art panty liner structure.
Figure 2:
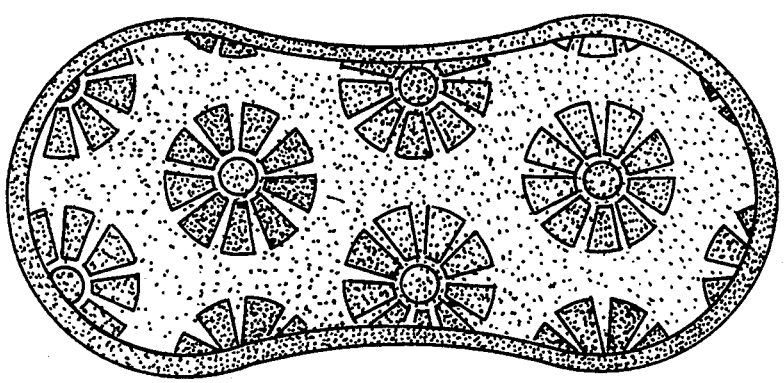
FIG. 2 is an orthographic top view of a prior art insert liner.
Figure 3:
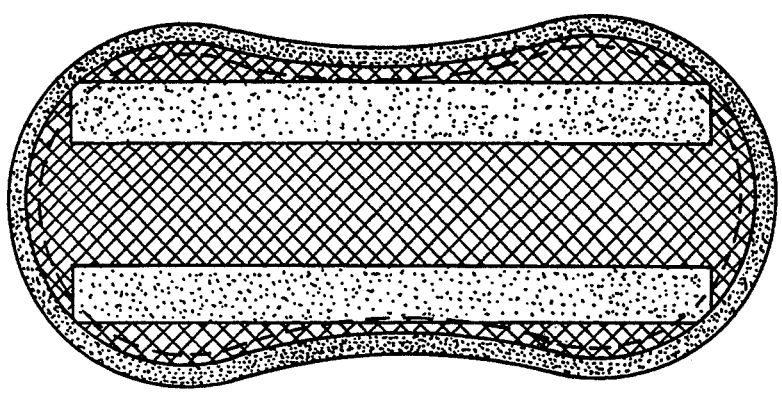
FIG. 3 is an orthographic bottom view of the prior art insert for an associated panty garment.

With reference now to the drawings, and in particular to FIGS. 1 to 11 thereof, a new and improved fragrance insert panty undergarment embodying the principles and concepts of the present invention and generally designated by the reference numeral 10 will be described.

More specifically, the fragrance insert panty undergarment 10 of the instant invention essentially comprises a panty member 11 having a continuous body panel, to include a front panel 12 connected to a rear panel 13 by a crotch web 15. An elastomeric band 14 of continuous construction is mounted to an upper end of the body panel, with right and left leg openings 27 and 28 respectively directed through the body panel between the front and rear panels 12 and 13 respectively.

The crotch web 15 is formed of a porous fabric having a pocket 16 therewithin, in a manner as indicated in FIG. 4a, accessed through a pocket flap 17. The pocket flap 17 including a hook and loop fastener patch 18 mounted to the front panel 12 is cooperative with a second hook and loop fastener patch 19 mounted to the pocket flap 17. The pocket accordingly is arranged to receive an insert web 20 that is formed of a flexible fibrous fluid saturated pad formed of any desired commercially available fragrance.

A modified insert web 21 includes a contrasting coloration identification pad 22 mounted to the pad for ease of identification and selection of various pads for use. A flexible fluid conduit 23 is directed in fluid communication with the web 21 arranged for securement to a reservoir outlet tube 26 and an associated fluid reservoir tube 24 mounted coextensively to the elastomeric band 14. A fill cap 25 directed into the reservoir tube 24 permits selective replenishment of fluid within the reservoir tube to direct fluid in a metered relationship through the reservoir tube 24 into the associated web 21 that permits imparting of such fluid through the porous fabric crotch web 15 from the fibrous pad structure 21.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A fragrance insert panty undergarment, comprising, a panty member having a continuous body panel formed with a front panel spaced from a rear panel, with the front panel and the rear panel interconnected by a porous fabric crotch web, and the body panel including a continuous elastomeric band at an upper terminal end of the body panel, and a right leg opening and a left leg opening directed through the body panel between the front panel and the rear panel on opposed sides of the crotch web, and the crotch web including a pocket cavity, and the pocket cavity having a pocket flap, and the pocket flap includes a first hook or loop fastener patch and the front panel includes a second loop or hook fastener patch corresponding to said first patch, respectively, with the first fastener patch securable to the second fastener patch to permit enclosure of the pocket cavity, and an insert web received within the pocket cavity, and the insert web is formed of a flexible fibrous fluid saturated pad, and the insert web having a contrasting coloration identification pad mounted to the insert web for identification of the insert web, and the elastomeric band includes a fluid reservoir tube secured coextensively to the elastomeric band and the reservoir tube having a fill cap to permit directing of fluid within the reservoir tube, and the reservoir tube in fluid communication with a reservoir outlet tube, and a fluid conduit, the fluid conduit having a first end received within the reservoir outlet tube, and a second end directed into the insert web to direct fluid from the reservoir tube into the insert web.

* * * * *